United States Patent [19]

Collinson et al.

[11] Patent Number: 5,439,451
[45] Date of Patent: Aug. 8, 1995

[54] CAPLESS MEDICAL BACKCHECK VALVE

[75] Inventors: Michael Collinson; Alan K. Plyley; Russell J. Redmond, all of Goleta; Claude Vidal, Santa Barbara, all of Calif.

[73] Assignee: B. Braun Medical, Inc., Allentown, Pa.

[21] Appl. No.: 351,206

[22] Filed: Nov. 30, 1994

Related U.S. Application Data

[63] Continuation of Ser. No. 215,783, Mar. 22, 1994.

[51] Int. Cl.⁶ .............................................. A61M 5/00
[52] U.S. Cl. .................... 604/247; 604/256; 137/614.18
[58] Field of Search ................ 604/283, 284, 247, 86, 604/87, 83, 256, 905, 82, 83, 249; 137/514.18, 614.19

[56] References Cited

U.S. PATENT DOCUMENTS 3,570,484  3/1971  Steer .
3,831,629  8/1974  Mackal et al. .
4,429,856  2/1984  Jackson .
5,006,114  4/1991  Rogers et al. .
5,049,128  9/1991  Duquette .
5,147,333  9/1992  Raines .
5,201,725  4/1993  Kling .
5,242,432  9/1993  Defrank .
5,284,475  2/1994  Mackal .
5,353,837  10/1994  Faust .

Primary Examiner—John D. Yasko
Attorney, Agent, or Firm—Shoemaker and Mattare, Ltd.

[57] ABSTRACT

A medical backcheck valve includes a hollow housing containing an upwardly biased piston assembly for controlling liquid flow therethrough. The piston assembly comprises a substantially rigid plug having one end protruding from the upper end of the housing, and a flexible sheath covering having a relatively small diameter upper end surrounding the plug, a main seal for controlling flow through said first flow space, and a tubular lower end, secured at the bottom of the housing, for preventing liquid from entering within the covering.

19 Claims, 6 Drawing Sheets

CAPLESS MEDICAL BACKCHECK VALVE this is a continuation of application Ser. No. 08/215,783, filed Mar. 22, 1994 pending.

BACKGROUND OF THE INVENTION

This invention relates generally to fluid handling, and more particularly to a check valve for medical uses.

So-called needless injection ports, installed in infusion lines, provide sites where supplemental medication or other fluids may be introduced into the infusion line. Such ports actually contain quick-connect valves which close automatically when the medication syringe or line is withdrawn from the valve.

Representative prior U.S. Patents include U.S. Pat. Nos. 3,570,484, 3,831,629, 5,006,114, 5,049,128, 5,147,333, 5,201,725 and 5,242,432.

A needleless injection port must, of course, be and remain sanitary. It cannot admit air or other fluids accidentally, and must not drip or leak, either in use, or thereafter. It would be best to isolate moving parts of an injection port, as much as possible, from liquids flowing therethrough, and to provide a vent for gases in the valve, to prevent pressure differentials from occurring between the fluids (air and liquid) within the valve.

To prevent leakage, we surrounded all the moving parts of an injection port valve with an elastomeric sheath, constraining fluid to flow through the device only outside the sheath. This approach has the advantages of positively preventing liquid-air leaks, by eliminating sliding piston seals, but it creates a closed volume within the sheath which has to be vented, to prevent air pressure from being developed as the valve opens. The problem of venting is also addressed by this invention.

SUMMARY OF THE INVENTION

All object of the invention is to provide a simple yet reliable check valve for use in medical infusion lines and the like.

Another object of the invention is to prevent leakage into or out of all infusion line when the valve is inactive, while providing a valve with an exposed surface which, upon depression by the tip of a syringe, operas a flow path into the line.

These and other objects are attained by a medical backcheck valve including a hollow housing containing an upwardly biased piston assembly for controlling liquid flow therethrough. The piston assembly comprises a substantially rigid plug having one end protruding from the upper end of the housing, and a tubular flexible covering having a relatively small diameter upper end surrounding the plug, a main seal for controlling flow through said first flow space, and a tubular lower end, secured at the bottom of the housing, for preventing liquid from entering within the covering.

BRIEF DESCRIPTION OF THE DRAWINGS

In the accompanying drawings.

DESCRIPTION OF THE PREFERRED EMBODIMENT

Figure 1:
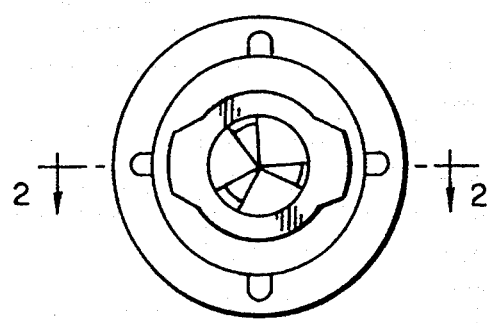
FIG. 1 is a top plan view of a valve embodying the invention.
Figure 5:
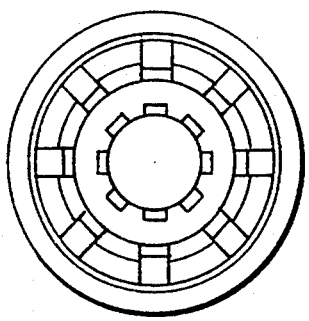
FIG. 5 is a bottom plan view of only the valve housing.
Figure 6:
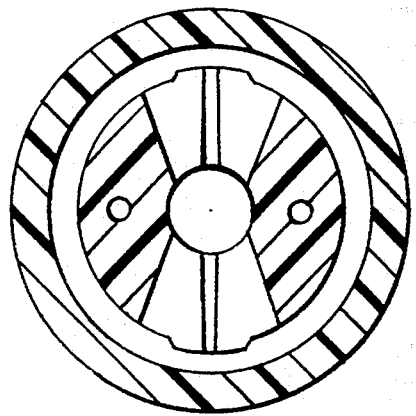
FIG. 6 is a horizontal section taken through the fitting only on the plane 6—6 in FIG. 1.

A medical backcheck valve embodying the invention includes an outer housing 10 (FIGS. 1–4) made by injection molding a rigid thermoplastic, such as a polycarbonate. The housing has a tubular upper section 12 of a first diameter, and a lower section 14 of a larger second diameter. The outer surface of the housing has a smooth transition 16 (FIG. 2) between the upper and lower sections. The lower section has a circumferential flange 18 of a third, even larger diameter at its bottom. Ribs on the outside of the housing improve handling.

Inside, the housing has a slightly tapered inlet bore 20 at its upper end, a larger main bore 22 within the lower section, and a counterbore 24 at the bottom, defined by the flange. Eight equally spaced axially extending upper recesses 26 in the transition area serve as flow channels, and there are eight lower axial grooves 28 on the inner surface of the main bore.

A flexible elastomeric piston 30, reinforced with a rigid plastic plug 32, is installed into the housing from the bottom, and retained therein by a plastic luer nut fitting 34 which is secured the counterbore by welding or adhesive.

The fitting comprises a downwardly tapering fluid port 36 surrounded by an internally threaded skirt 38; together these serve as a female luer nut. The peripheral rim 40 just above the skirt is joined to the housing by welding or an adhesive. Above the rim is a base portion 42 of reduced diameter, surrounded by an annular gap or plenum 44 which communicates with the space around the piston via the grooves 28. Four liquid passages 46 extend radially from the top of the port to the plenum. To allow air to escape from the valve, there are two axially extending vent holes 48 which pass between, but do not intersect, the liquid passages. Each vent hole terminates within the space 50 between the skirt and the port.

Figure 2:
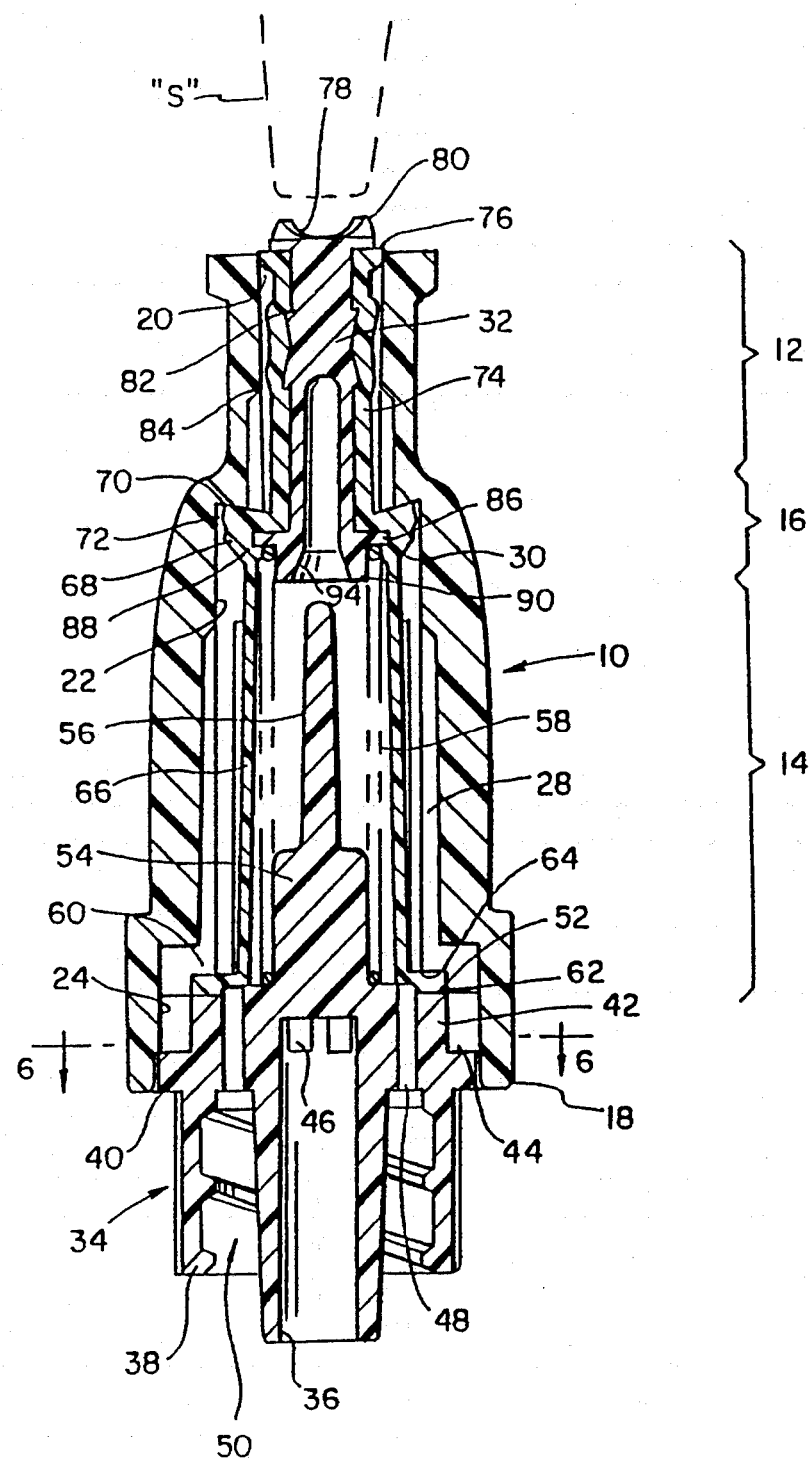
FIG. 2 is a sectional view of the valve, closed, on a vertical axial plane (designated 2—2 in FIG. 1)
Figure 3:
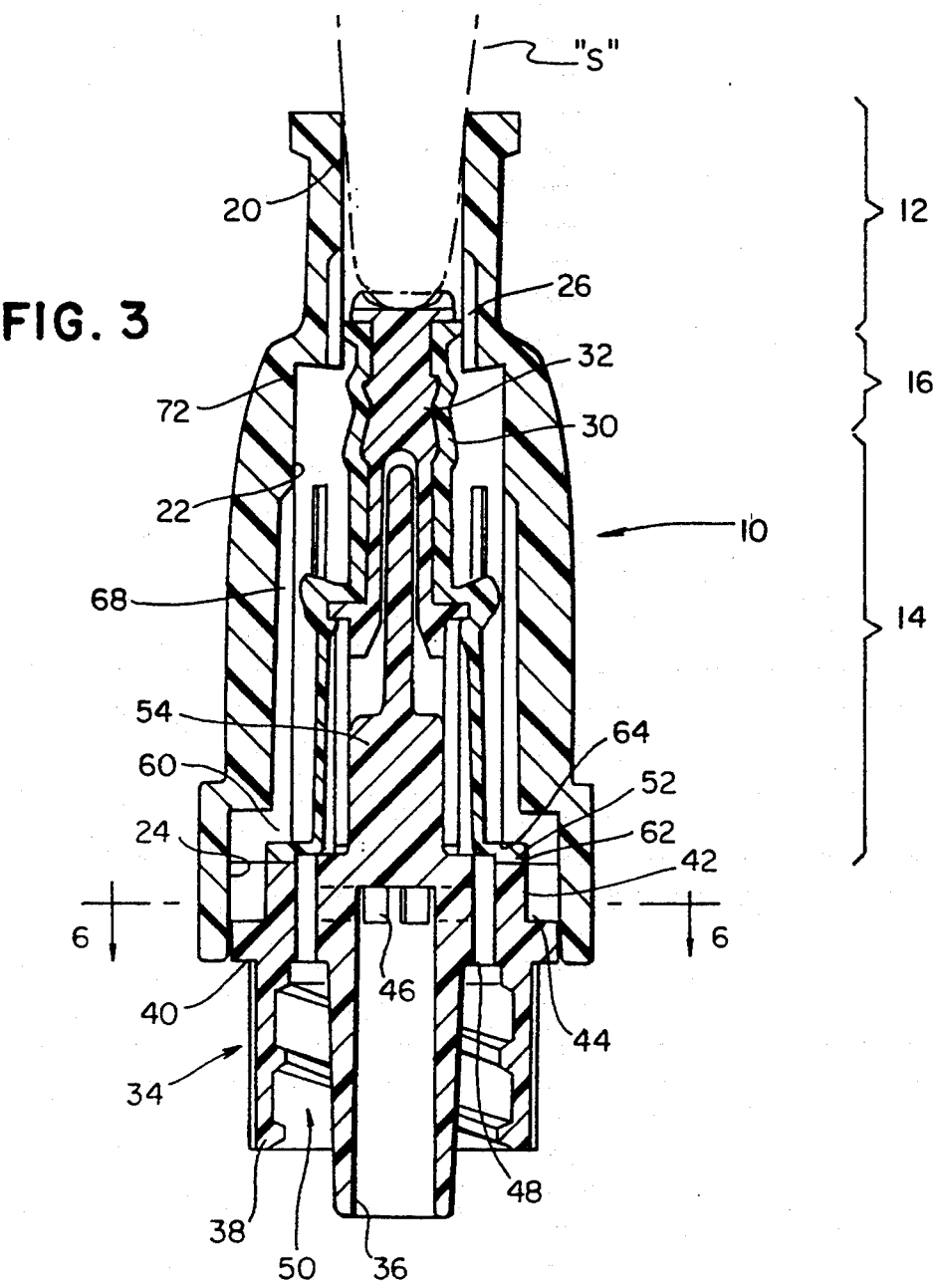
FIG. 3 shows the valve of FIG. 2 open.

Looking closely at FIG. 2, one can see that the top surface of the base portion of the fitting is peripherally undercut to form an annular seat 52 extending just outside the tops of the vent holes.

Rising from the base, at is center, is a centering post 54 having a small-diameter tip 56. The cross-section of the post is "X"-shaped (see FIG. 4), to reduce its mass. The function of the post is to center a stainless compression spring 58, while the tip centers the piston plug when the valve is open.

The silicone rubber piston member is a surface of revolution. At its lower end is a circular foot 60 having an enlarged circumferential bead 62 that is permanently clamped between the seat at the top of the fitting base and an undercut 64 at the bottom of the main bore. The bead thus prevents liquid from entering the interior area occupied by the spring. The thin, flexible tubular wall 66 of the piston above the foot is bounded above by a thickened main seal 68. The upper surface of this seal, seen in detail in FIG. 4, includes a rounded lip 70 which contacts the bottom surface of a conical shoulder 72 formed inside the body near the transition, when the valve is closed. Above the main seal, the piston has a smaller-diameter tubular section 74 terminating at an out-turned flange 76 forming an auxiliary seal.

The plug, forced into the piston from its lower end before the piston assembly is inserted into the housing, has a dished top 78 with three (illustrated) or more spaced protuberances 80 that prevent this surface from occluding or blocking the end of a syringe tip "S" (FIG. 3) or the like pushed against it to open the valve. Each protuberance is essentially a wedge whose upper face is a portion of a common spherical surface.

Below the top of the plug, there are a pair of circumferential barbs 82,84 for retaining the plug within the piston. At the bottom, the plug has a flange 86 that snaps into a groove 88 in the main seal. This flange also serves as a seat for the upper end of the compression spring, which is kept centered by a collar 90 at the bottom of the plug. A blind bore 92, having a flared mouth 94 opening downwardly, is provided at the bottom end of the plug. The bore is slightly larger than the tip of the lower centering post described previously.

Figure 4:
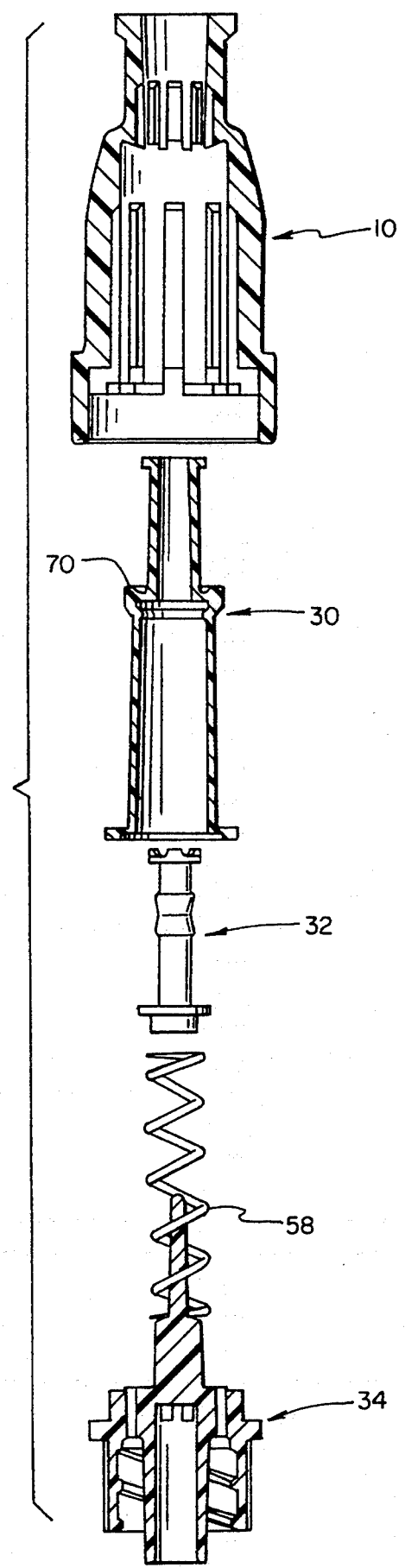
FIG. 4 is an exploded side elevation of the valve, showing its five components prior to assembly.

During assembly, as suggested by FIG. 4, the plug is first forced into the rubber piston (alternatively, it could be insert molded to the piston); then that assembly is inserted into the bottom of the housing. Finally, the spring and the fitting are inserted, and the fitting is permanently attached to the housing.

The valve described above is normally kept closed (FIG. 2) by the spring force. However, one can open the valve by inserting the tip "S" of a syringe (as in FIG. 3), or other appropriately sized conduit, into the tapered bore at the top of the housing. Doing so depresses the piston plug, and unseats the main seal. The plug must be moved sufficiently far, however, so that the auxiliary seal unseats, before liquid begins to flow from the syringe tip into the housing.

As the plug is depressed, the tip enters into the bore, keeping the plug centered, so that the sides of the piston do not drag on the main bore of the housing, and so that the piston seats properly when the syringe tip is removed.

Air escapes through the vent holes in the fitting as the piston is depressed.

Interference between the tip 56 and the bottom of the bore 92 limits downward movement of the plug.

The recesses and grooves mentioned above keep the main and auxiliary seals from blocking the flow path, which is depicted by arrows in FIG. 2. They also keep the flaccid compressed tubular portion of the piston from blocking flow. Note that the fitting serves as a cross-over so that the inner volume above the fitting communicates with the outer volume below it, and vice-versa.

Because the tubular lower portion 66 of the piston is thin, it can expand and contract radially. In its intended medical environment, working pressures are not large. In any event, compression and expansion of the sheath are limited by the compression spring, and the main bore of the housing, respectively.

Figure 7:
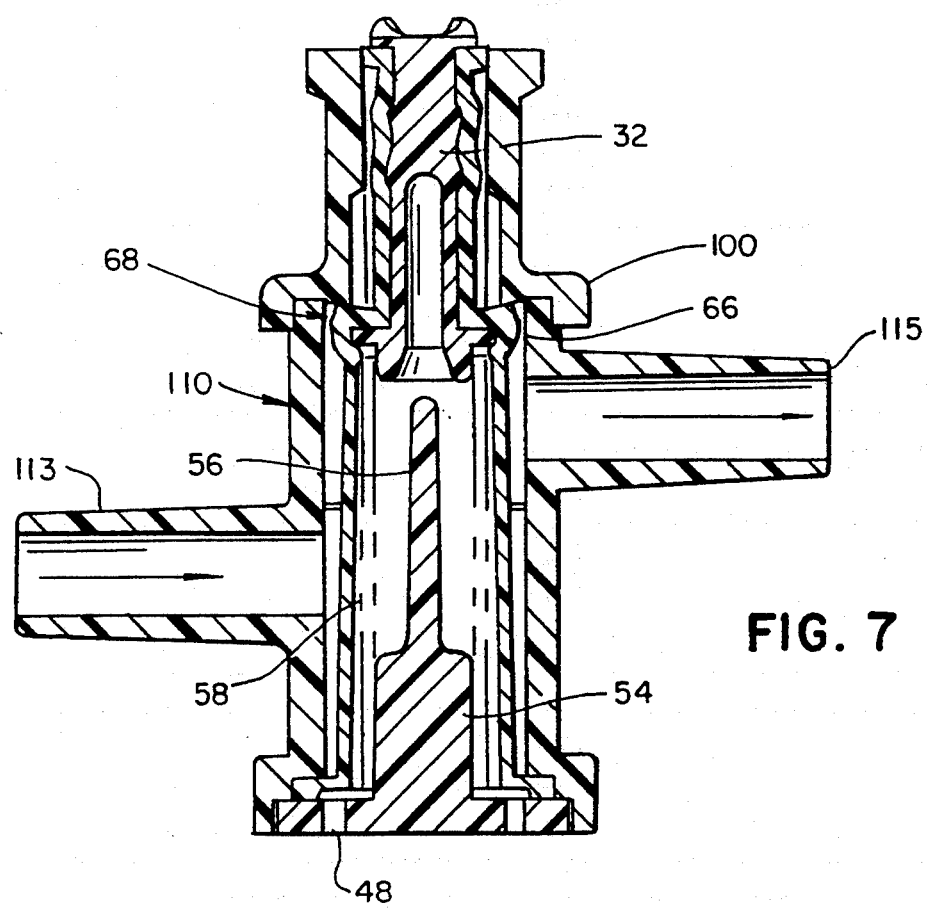
FIG. 7 is a view, corresponding to FIG. 2, of a modified form of the invention.

An alternative form of the invention is shown in FIG. 7. The piston 66 and its plug 32 are identical to that described above, but the fitting has been replaced by a simpler closure having air vent ports 48, as in the other embodiment, but lacking liquid channels. The centering post 54 and tip 56 are the same. In this embodiment, the housing has been replaced by a two-piece structure, the upper portion 100 of which terminates at the level of the main seal seat. The lower portion 110 has a pair of laterally extending offset inlet and outlet ports 113,115.

When the valve is pushed fully open, the main seal 68 blocks the normal flow path between the inlet and outlet ports, allowing only fluid from the syringe tip to pass to the outlet.

Figure 8:
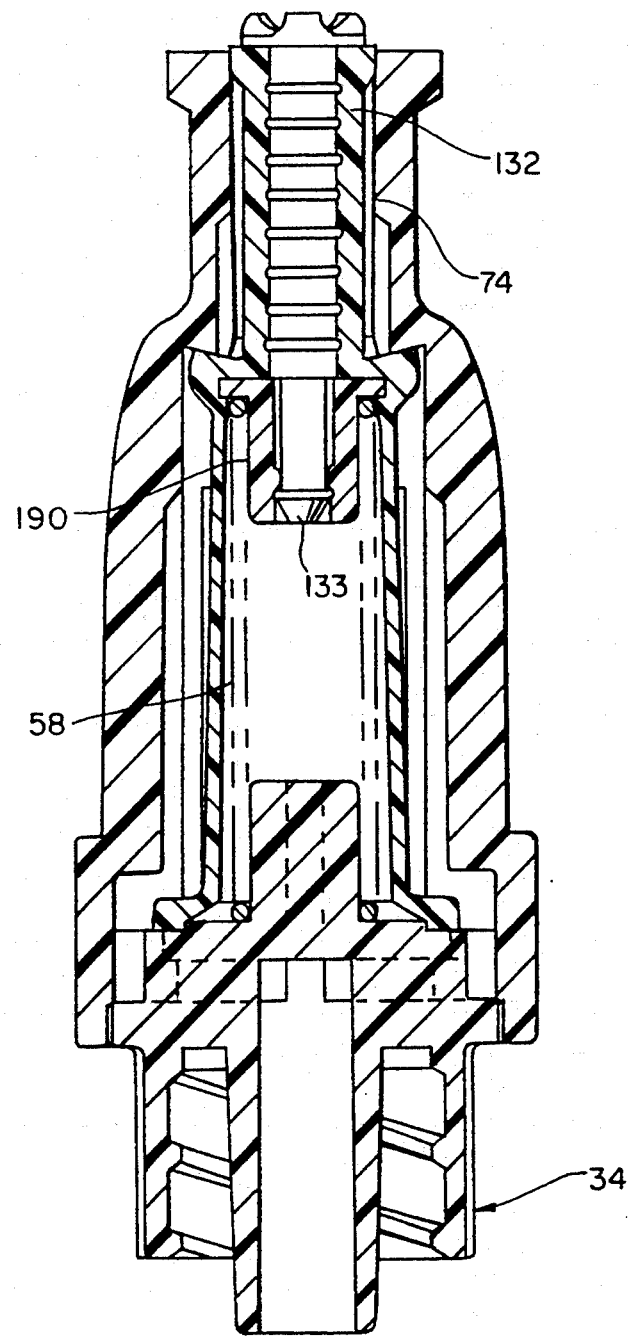
FIG. 8 is a view, like FIG. 2, of yet another form of the invention.

The valve depicted in FIG. 8 is like that of FIG. 2, except for the structure of the plug and the centering post. The modified plug is a two-piece assembly comprising a body portion 132 and a collar 190. The collar has a through-bore with a circumferential rib near its bottom end. A head 133, having a diameter slightly larger than the rib, is formed at the bottom of the plug. The collar is pushed over the head during assembly of the valve, and is securely retained by all annular shoulder defining the head.

In the above description and the claims that follow, words descriptive of orientation (upper, bottom, etc.) are provided to clarify the disclosure of the invention. They refer to the orientation shown in the drawings. However, it should be understood that the valve may be used in any orientation.

Preferred materials for various parts of the invention are identified above, to reveal the best mode of the invention and to enable others to make and use it. Nevertheless, it is expected that other materials may prove suitable, or even superior; the invention is not limited to particular materials.

Since the invention is subject to modifications and variations, it is intended that the foregoing description and the accompanying drawings shall be interpreted as illustrative of only one form of the inventions, whose scope is to be measured by the following claims.

I claim:

1. A medical backcheck valve comprising
a hollow housing having an upper end and a lower end,
a fitting secured within the lower end of the housing,
a piston assembly contained within the housing for controlling liquid flow therethrough,
said piston assembly comprising a substantially rigid plug having one end protruding from the upper end of the housing, and a tubular flexible covering having a relatively small diameter upper end surrounding the plug, with a first flow space between the housing and the sheath, a main seal for controlling flow through said first flow space, and a tubular lower end whose bottom is secured to at least one of the fitting and the housing to prevent liquid from entering within the tubular flexible covering.

2. The invention of claim 1, further comprising a vent hole extending through the fitting and providing communication between ambient air and the interior of the tubular flexible covering.

3. The invention of claim 1, wherein the housing has an internal shoulder functioning as a valve seat, and the tubular flexible covering is formed with art integral sealing lip that bears against time seat in the closed position of time piston, to prevent liquid from flowing through said first flow space.

4. The invention of claim 3, wherein said shoulder faces downward, said lip is a circumferential lip facing said shoulder, and said closed position is the uppermost position of the piston.

5. The invention of claim 4, wherein the seat is a conical surface facing away from the axis of the housing, and the lip is formed on a thickened portion of the sheath having an upwardly dished surface.

6. The invention of claim 5, wherein the plug has a circumferential flange within said thickened portion, supporting said lip.

7. The invention of claim 4, further comprising a spring for biasing said piston toward its closed position.

8. The invention of claim 7, wherein said spring is a compression coil spring whose upper end bears against said plug, and whose lower end bears against said fitting.

9. The invention of claim 8, wherein said fitting has an upward projecting post for centering said spring within the housing.

10. The invention of claim 9, further comprising a tip extending upward from said post, and said plug having an internal blind bore, open at the bottom, into which the tip enters when the plug is moved downward, to keep the piston centered within the housing.

11. The invention of claim 3, further comprising a second flow passage around the tubular flexible covering, below said lip, whereby the lip controls flow between said first and second flow spaces.

12. The invention of claim 11, wherein the fitting has means defining a liquid outlet port, and at least one passage extending between the outlet port and said second flow space.

13. The invention of claim 12, wherein the fitting has at least one air vent hole extending between ambient air and the interior of said tubular flexible covering, said vent hole being isolated from said passage.

14. The invention of claim 13, wherein said housing has a counterbore at its lower end, said fitting being secured in the counterbore, and the fitting having a portion of lesser diameter within the counterbore, defining an annular plenum, said passage extending between the outlet port and the plenum, and the plenum communicating with the second flow space.

15. The invention of claim 14, wherein said second flow space includes at least one axially extending groove formed on the interior of the housing, to prevent the tubular flexible covering from occluding the flow space.

16. The invention of claim 14, wherein the tubular flexible covering has a peripherally extending sealing flange at its lower end, said flange being clamped between an upper surface of said fitting and a shoulder at the top of said counterbore.

17. The invention of claim 3, wherein said housing has inlet and outlet ports, extending on offset transverse axes from opposite sides of said body, and said piston is movable from said closed position to a second position where the lip is below both said axes.

18. The invention of claim 1, wherein said plug comprises a body portion insertable into the tubular flexible covering from above and a collar insertable into the tubular from below, said collar having a through bore containing an internally protruding rib and said plug having a head slightly larger in diameter than said rib, but capable of passing through said bore, whereby the collar is retained on the plug by said internal rib.

19. The invention of claim 18, wherein the body portion of the plug has external circumferential ribs for retaining the tubular flexible covering thereon.

* * * * *